United States Patent
Wiedmann et al.

(10) Patent No.: US 9,952,164 B2
(45) Date of Patent: Apr. 24, 2018

(54) PHOTON-COUNTING CT-SYSTEM WITH REDUCED DETECTOR COUNTING-RATE REQUIREMENTS

(71) Applicant: General Electric Company, Schenectady, NY (US)

(72) Inventors: Uwe Wiedmann, Niskayuna, NY (US); Daniel David Harrison, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 334 days.

(21) Appl. No.: 13/724,376

(22) Filed: Dec. 21, 2012

(65) Prior Publication Data

US 2014/0177786 A1 Jun. 26, 2014

(51) Int. Cl.
G01N 23/06 (2018.01)
G01N 23/083 (2018.01)
G01N 23/04 (2018.01)

(52) U.S. Cl.
CPC .......... *G01N 23/046* (2013.01); *G01N 23/06* (2013.01); *G01N 23/083* (2013.01); *G01N 2223/419* (2013.01); *G01N 2223/423* (2013.01); *G01N 2223/612* (2013.01)

(58) Field of Classification Search
CPC ............ G01N 23/06; A61B 6/032; A61B 6/58
USPC .............................................. 378/98.9, 98.1
See application file for complete search history.

(56) References Cited

U.S. PATENT DOCUMENTS

| 3,515,874 | A | * | 6/1970 | Bens | A61B 6/502 378/143 |
|---|---|---|---|---|---|
| 4,260,885 | A | * | 4/1981 | Albert | 378/45 |
| 4,442,489 | A | * | 4/1984 | Wagner | A61B 6/032 378/19 |
| 5,155,365 | A | | 10/1992 | Cann et al. | |
| 6,069,936 | A | * | 5/2000 | Bjorkholm | 378/98.9 |
| 6,269,144 | B1 | | 7/2001 | Dube et al. | |
| 7,260,171 | B1 | | 8/2007 | Arenson et al. | |
| 7,298,812 | B2 | | 11/2007 | Tkaczyk et al. | |
| 7,551,712 | B2 | | 6/2009 | Shaughnessy | |
| 7,792,241 | B2 | | 9/2010 | Wu et al. | |
| 8,160,200 | B2 | | 4/2012 | Tkaczyk et al. | |
| 8,165,264 | B2 | | 4/2012 | Zou | |
| 2005/0195939 | A1 | * | 9/2005 | Scheinman | G01N 23/046 378/57 |
| 2007/0165772 | A1 | * | 7/2007 | Sainath et al. | 378/7 |

(Continued)

OTHER PUBLICATIONS

Taguchi et al., "Enabling Photon Counting Clinical X-Ray CT", Nuclear Science Symposium Conference Record (Nss/Mic), 2009 IEEE, Issue Date : Oct. 24, 2009-Nov. 1, 2009, pp. 3581-3585, ISSN :1095-7863.

*Primary Examiner* — Jason McCormack
*Assistant Examiner* — James Choi
(74) *Attorney, Agent, or Firm* — Pabitra K. Chakrabarti

(57) ABSTRACT

Various of the disclosed embodiments contemplate systems and methods that compensate for the limited dynamic range of certain X-Ray detector systems, such as CAT-Scan detector systems. In some embodiments, the system alternates between different photon emission flux values and then gives more consideration to an attenuation value associated with a more favorable detection flux. In this manner, different object densities may be accounted for and may be more properly imaged despite the particular characteristics of the X-Ray system.

12 Claims, 7 Drawing Sheets

(56) References Cited

U.S. PATENT DOCUMENTS

| | | | |
|---|---|---|---|
| 2007/0183560 A1* | 8/2007 | Popescu et al. | 378/5 |
| 2008/0101544 A1 | 5/2008 | Wies et al. | |
| 2008/0260094 A1* | 10/2008 | Carmi | 378/19 |
| 2010/0282972 A1* | 11/2010 | Carmi | G01T 1/2928 250/362 |
| 2011/0168878 A1* | 7/2011 | Hoerndler | A61B 6/583 250/252.1 |
| 2012/0121063 A1* | 5/2012 | Proksa | 378/16 |
| 2012/0236995 A1* | 9/2012 | Eusemann | A61B 6/03 378/108 |

\* cited by examiner

PHOTON-COUNTING CT-SYSTEM WITH REDUCED DETECTOR COUNTING-RATE REQUIREMENTS

BACKGROUND

X-ray computed tomography imaging, also referred to as computed tomography (CT-scan) or computed axial tomography (CAT scan), employs computer-processed X-ray projections to generate images of the interior of an object of interest. Theses systems generally successively emit and detect photons in the X-ray energy range, directed toward an object, so as to generate a plurality of consecutive cross-sectional projection images of the object's contents. These cross-sectional projections may then be used to generate a three-dimensional image of the inside of the object. The three-dimensional image may be used for diagnostic and therapeutic purposes in various medical disciplines, but may also be used in a wide variety of other contexts, such as baggage inspection.

CT-scan photon detection systems, and certain X-ray detector systems in general, may occasionally possess unique limitations or characteristics that adversely affect the system's ability to image certain portions of a patient or other object. Rather than ignore or only incompletely address these limitations, there exists a need for an X-ray imaging system which can continue to retrieve accurate data, despite the detector having these various limitations.

SUMMARY

Certain embodiments contemplate a method to accommodate detector behavior when generating at least a portion of an X-ray image comprising: emitting a first plurality of photons; collecting at a detector at least some of the first plurality of photons at a first detection flux; emitting a second plurality of photons; collecting at the detector at least some of the second plurality of photons at a second detection flux, wherein the second detection flux is greater than the first detection flux; determining a first relation between the first detection flux and a reference flux; determining a second relation between the second detection flux and a reference flux; and generating at least a portion of an X-ray image based on the first relation and the second relation.

In some embodiments, determining a first relation between the first detection flux and a reference flux comprises calculating a first quality value and wherein determining a second relation between the second detection flux and a reference flux comprises calculating a second quality value. In some embodiments, generating at least a portion of an X-ray image comprises: determining a first attenuation value associated with the first detection flux; determining a second attenuation value associated with the second detection flux; and calculating an output attenuation value based on the first and second attenuation values and the first and second quality values. In some embodiments, the detector is configured to experience: photon pileup at a high detection flux, the high detection flux greater than the reference flux; and a signal to noise ratio at a low detection flux less than a signal to noise ratio at the reference flux, the low detection flux less than the reference flux. In some embodiments, generating at least a portion of an X-ray image comprises using the at least some of the first plurality of photons to generate an attenuation value if the first detection flux falls within a range.

In some embodiments, the first plurality of photons each have generally a first mean energy and the second plurality of photons each have generally a second mean energy. In some embodiments, the first plurality of photons are emitted using a first voltage and the second plurality of photons are emitted using a second voltage, the first voltage different from the second voltage. In some embodiments, the first plurality of photons are emitted using a first current and the second plurality of photons are emitted using a second current, the first current different from the second current. In some embodiments, emitting the first plurality of photons comprises applying a source attenuator in a first configuration and emitting the second plurality of photons comprises applying the source attenuator in a second configuration, the second configuration different from the first configuration. In some embodiments, the method further comprises beginning the collection of the at least some of the second plurality of photons before increasing a current associated with emitting the second plurality of photons. In some embodiments, the method further comprises stopping the collection of the at least some of the second plurality of photons after decreasing a current associated with emitting the second plurality of photons. In some embodiments, the second plurality of photons is emitted before the first plurality of photons is emitted. In some embodiments, the method further comprises determining a first relation between the first detection flux and a reference flux comprises determining whether the first detection flux falls within a range; determining a second relation between the second detection flux and the reference flux comprises determining whether the second detection flux falls within the range; and wherein generating at least a portion of an X-ray image based on the first relation and the second relation comprises generating at least a portion of the X-ray image based on a first attenuation value associated with the first detection flux if the first detection flux falls within the range and generating at least a portion of the X-ray image based on a second attenuation value associated with the second detection flux if the second detection flux falls within the range. In some embodiments, determining a first relation between the first detection flux and a reference flux comprises determining a first weighting factor based on a difference between the first flux and a reference flux, wherein determining a second relation between the second detection flux and a reference flux comprises determining a second weighting factor based on a difference between the second flux and a reference flux, and wherein generating at least a portion of an X-ray image comprises determining a final attenuation value, the final attenuation value based on a first attenuation value associated with the first detection flux weighted by the first weighting factor and a second attenuation value associated with the second detection flux weighted by the second weighting factor.

Certain embodiments contemplate a non-transitory computer-readable medium comprising instructions configured to cause one or more processors to cause a system to: emit a first plurality of photons; collect at a detector at least some of the first plurality of photons at a first detection flux; emit a second plurality of photons; collect at the detector at least some of the second plurality of photons at a second detection flux, wherein the second detection flux is greater than the first detection flux; determine a first relation between the first detection flux and a reference flux; determine a second relation between the second detection flux and a reference flux; and generate at least a portion of an X-ray image based on the first relation and the second relation.

In some embodiments, generating at least a portion of an X-ray image comprises using the at least some of the first plurality of photons to generate an attenuation value if the first detection flux falls within a range. In some embodiments, the first plurality of photons comprises a first group of photons each have generally a first mean energy and a second group of photons each have generally a second mean energy. In some embodiments, determining a first relation between the first detection flux and a reference flux comprises determining whether the first detection flux falls within a range; determining a second relation between the second detection flux and the reference flux comprises determining whether the second detection flux falls within the range; and wherein generating at least a portion of an X-ray image based on the first relation and the second relation comprises generating at least a portion of the X-ray image based on a first attenuation value associated with the first detection flux if the first detection flux falls within the range and generating at least a portion of the X-ray image based on a second attenuation value associated with the second detection flux if the second detection flux falls within the range.

Certain embodiments contemplate a system to accommodate detector behavior when generating at least a portion of an X-ray image comprising: a first X-ray source configured to emit a first plurality of photons; a second X-ray source configured to emit a second plurality of photons, the second plurality of photons comprising more photons than the first plurality of photons; a first detector configured to receive at least some of the first plurality of photons; a second detector configured to receive at least some of the second plurality of photons; a first flux determiner configured to determine a first flux at which the at least some of the first plurality of photons are collected at the first detector; a second flux determiner configured to determine a second flux at which the at least some of the second plurality of photons are collected at the second detector; one or more computer systems configured to: determine a first relation between the first detection flux and a reference flux; determine a second relation between the second detection flux and a reference flux; and generate at least a portion of an X-ray image based on the first relation and the second relation.

In some embodiments, at least one of the first detector and the second detector is configured to experience: photon pileup at a high detection flux, the high detection flux greater than the reference flux; and a signal to noise ratio at a low detection flux less than a signal to noise ratio at the reference flux, the low detection flux less than the reference flux. In some embodiments, the first X-Ray source and the second X-Ray source are the same X-Ray source, the first detector and the second detector are the same detector, and the first flux determiner and the second flux determiner are the same flux determiner. In some embodiments, the first plurality of photons each have generally a first mean energy and the second plurality of photons each have generally a second mean energy. In some embodiments, determining a first relation between the first detection flux and a reference flux comprises determining whether the first detection flux falls within a range; determining a second relation between the second detection flux and the reference flux comprises determining whether the second detection flux falls within the range; and wherein generating at least a portion of an X-ray image based on the first relation and the second relation comprises generating at least a portion of the X-ray image based on a first attenuation value associated with the first detection flux if the first detection flux falls within the range and generating at least a portion of the X-ray image based on a second attenuation value associated with the second detection flux if the second detection flux falls within the range.

Any combination or permutation of embodiments is envisaged. Other objects and features will become apparent from the following detailed description considered in conjunction with the accompanying drawings. It is to be understood, however, that the drawings are designed as an illustration only and not as a definition of the limits of the invention.

DESCRIPTION OF EXEMPLARY EMBODIMENTS

In exemplary embodiments, an X-ray imaging system, such as a CT system, may switch between a high source flux and a low source flux configuration to anticipate the non-ideal saturation behavior in a detector. Particularly, the system may exclude or minimize the influence of photon counts at a detector cell when the corresponding detection flux falls outside a favorable region of the detector's capabilities. For example, where the detected flux of a low flux emission falls in a favorable region, but a detected flux of a high flux emission falls in an unfavorable region, the system may use the photon count received at the detector cell during the low flux emission to generate the photon count for the detector cell and the corresponding image value. The system may ignore, or give less effect, in this example to the photon count derived from the high flux detection. Certain embodiments do not apply a rigorous range boundary, but may permit gradations of influence for the photon counts at each flux.

As used herein, the "energy" of an X-ray photon is directly related to the associated electromagnetic "frequency" of the photon. A "flux" is a relation, such as a ratio, between the number of photons passing through a fixed region over a period of time. In some embodiments, the emission flux is a rate of photon emission in photons per steradian per second and detection flux is a rate of photon incidence on a detector in photons per second. Increasing current at the X-ray source will increase the number of emitted photons, while increasing the voltage at the X-ray source will increase the energy of the emitted photons.

Computed Tomography Scanner Overview

Figure 1A:
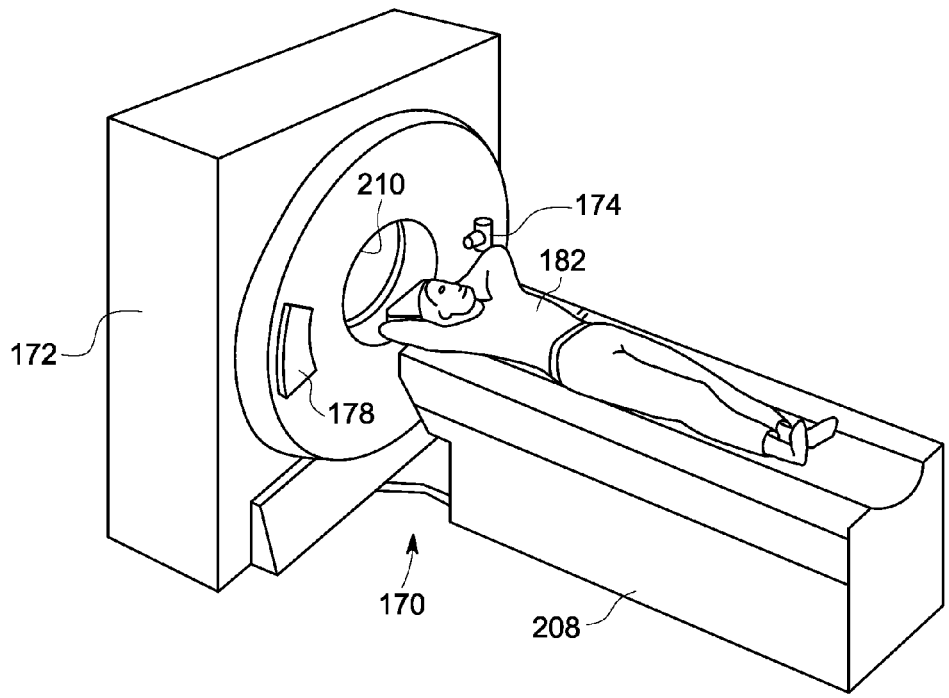
FIG. 1A is a pictorial view of a computed tomography (CT) imaging system in connection with which various embodiments may be implemented.
Figure 1B:
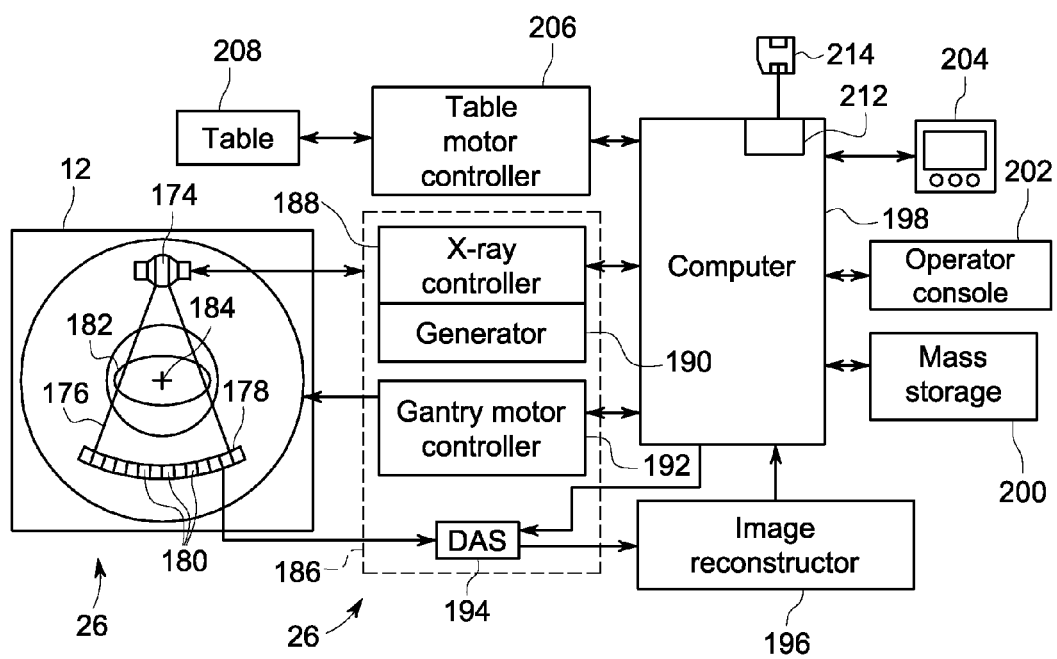
FIG. 1B is a block schematic diagram of the CT imaging system of FIG. 1A.

FIG. 1A is a pictorial view of a CT imaging system 170. FIG. 1B is a block schematic diagram of the system 170 illustrated in FIG. 1A. In the exemplary embodiment, the CT imaging system 170 is shown as including a gantry 172 representative of a "third generation" CT imaging system. The gantry 172 has an X-ray source 174 that projects a cone beam 176 of X-rays toward a detector array 178 on the opposite side of gantry 172. In some embodiments, X-ray source 174 is a Bremsstrahlung X-ray source.

The detector array 178 may be formed by a plurality of detector rows (not shown) including a plurality of detector elements 180 that together sense the projected X-ray beams that pass through an object, such as a medical patient 182 or piece of luggage. Each detector element 180 may produce an electrical signal that represents the intensity of an impinging X-ray radiation beam and hence is indicative of the attenuation of the beam as it passes through object or patient 182. The intensity may correspond to the number of incident photons at the element. An imaging system 170 having a multi-slice detector 178 may be capable of providing a plurality of images representative of a volume of object 182. Each image of the plurality of images corresponds to a separate "slice" of the volume. The "thickness" or aperture of the slice is dependent upon the height of the detector rows.

During a scan to acquire X-ray projection data, a rotating section within the gantry 172 and the components mounted thereon rotate about a center of rotation 184. FIG. 1B shows only a single row of detector elements 180 (i.e., a detector row). However, the multi-slice detector array 178 may include a plurality of parallel detector rows of detector elements 180 such that projection data corresponding to cone-beam geometry can be acquired simultaneously during a scan.

Rotation of components within the gantry 172 and the operation of radiation source 174 may be governed by a control mechanism 186. The control mechanism 186 includes an X-ray controller 188 and generator 190 that provides power and timing signals to the X-ray source 174 and a gantry motor controller 192 that controls the rotational speed and position of rotating portion of gantry 172. A data acquisition system (DAS) 194 in the control mechanism 186 samples analog data from detector elements 180 and converts the data to digital signals for subsequent processing. An image reconstructor 196 receives sampled and digitized measurement data from the DAS 194 and performs high-speed image reconstruction. The reconstructed image is applied as an input to a computer 198 that stores the image in a mass storage device 200. Although shown as a separate device, image reconstructor 196 may be special hardware located inside computer 198 or software executing within computer 198.

The computer 198 also receives commands and scanning parameters from an operator via a console 202 that has a keyboard and/or other user input device(s). An associated display system 204 allows the operator to observe the reconstructed image and other data from the computer 198. The operator supplied commands and parameters may be used by the computer 198 to provide control signals and information to the DAS 194, X-ray controller 188, generator 190 and gantry motor controller 192. In addition, the computer 198 operates a table motor controller 206 that controls a motorized table 208 to position the patient 182 in the gantry 172. The table 208 moves portions of the patient 182 through a gantry opening 210.

In one embodiment, the computer 198 includes a device 212, for example, a floppy disk drive, CD-ROM drive, DVD-ROM drive, or a solid state hard drive for reading instructions and/or data from a computer-readable medium 214, such as a floppy disk, CD-ROM, or DVD. It should be understood that other types of suitable computer-readable memory are recognized to exist (e.g., CD-RW and flash memory, to name just two), and that this description is not intended to exclude any of these. In another embodiment, the computer 198 executes instructions stored in firmware (not shown). Generally, a processor in at least one of the DAS 194, reconstructor 196, and computer 198 shown in FIG. 1B may be programmed to execute control commands to perform switching as described in more detail herein. The switching is not limited to practice in the CT system 170 and can be utilized in connection with many other types and variations of imaging systems. In one embodiment, the computer 198 is programmed to perform different functions to switch the switching devices described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 2:
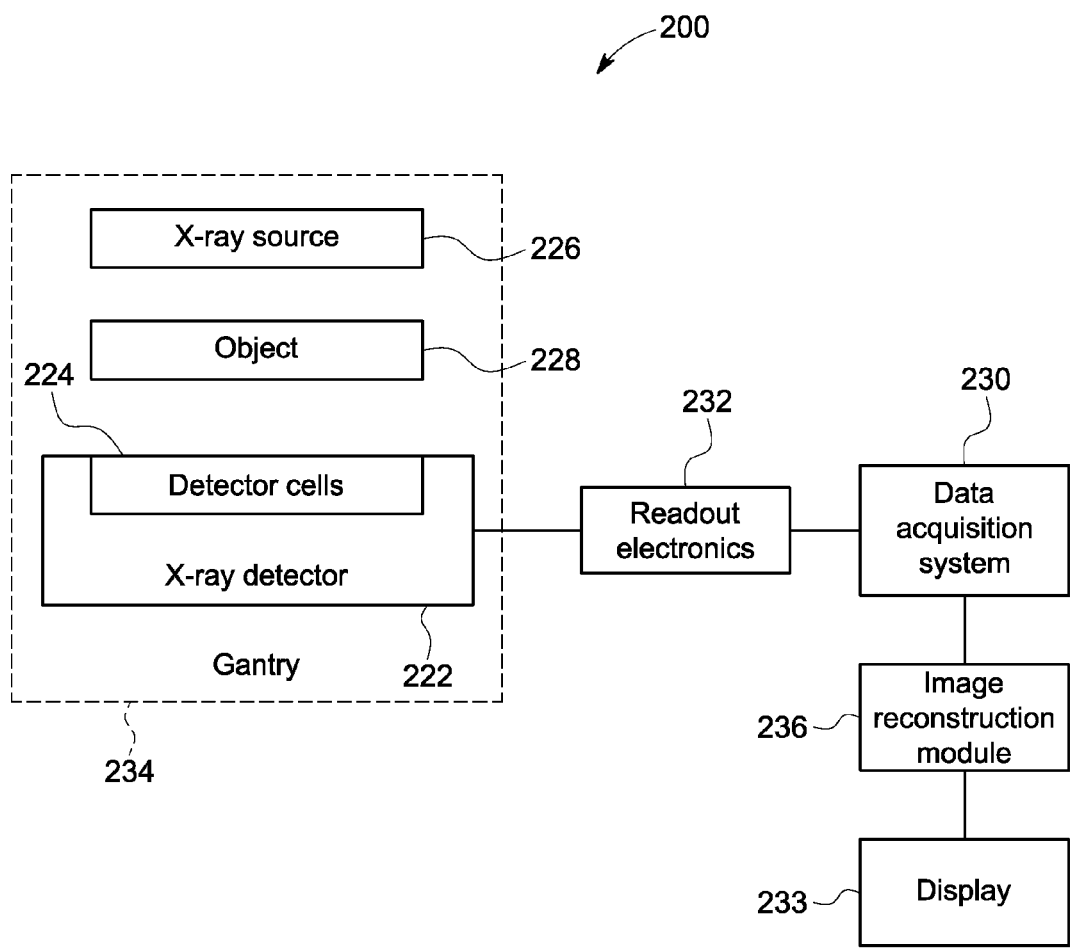
FIG. 2 is a schematic block diagram of an X-ray imaging system in connection with which various embodiments may be implemented.

FIG. 2 illustrates an X-ray imaging system 220 in which various embodiments may be implemented. The imaging system 220 generally includes an X-ray detector 222 having an array of detector cells 224 defining a scan area, and an X-ray source 226. Detector cells 224 may be the same as the elements 180 of the CT scanner of FIG. 1B in some embodiments. An object 228, such as a patient, is positioned between the X-ray source 226 and the X-ray detector 222, which may be one or more detectors or detector modules. However, the imaging system 220 may also scan other objects, such as in an industrial inspection application. The imaging system 220 also includes a data acquisition system 230 with readout electronics 232. Although shown separately in FIG. 2, the readout electronics 232 may reside within the X-ray detector 222 or the data acquisition system 230.

In one embodiment, the X-ray detector(s) 222 may be flat-panel detector systems such as an amorphous silicon flat panel detector or other type of digital X-ray image detector, such as a direct conversion detector as known to those skilled in the art. In another embodiment, the X-ray detector(s) 222 may include a scintillator having a screen that is positioned in front of the X-ray detector(s) 222.

It should be noted that the imaging system 220 may be implemented as a non-mobile or mobile imaging system. Moreover, the imaging system 220 may be provided in different configurations. For example, the image data may be generated with the X-ray source 226 positioned at discrete foci along an arc above the object to generate the image information using computed tomosynthesis procedures and processes (or maybe with the X-ray source in a radiographic configuration). In other embodiments, the X-ray source 226 and the X-ray detector 222 are both mounted at opposite ends of a gantry 234, which may be a C-arm that rotates about the object 228. The rotatable C-arm is a support structure that allows rotating the X-ray source 226 and the X-ray detector 222 around the object 228 along a substantially circular arc, to acquire a plurality of projection images of the object 228 at different angles (e.g., different views or projections) that are typically less than 360 degrees, but may comprise a full rotation in some circumstances.

In operation, the object 228 is positioned in the imaging system 220 for performing an imaging scan. For example, the X-ray source 226 may be positioned above, below or around the object 228. For example, the X-ray source 226 (and the X-ray detector(s) 222) may be moved between different positions around the object 228 using the gantry 234. X-rays are transmitted from the X-ray source 226 through the object 228 to the X-ray detector(s) 222, which detect X-rays impinging thereon.

The readout electronics 232 may include a reference and regulation board (RRB) or other data collection unit. The RRB may accommodate and connect data modules to transfer data (e.g., a plurality of views or projections) from the X-ray detector(s) 222 to the data acquisition system 230. Thus, the readout electronics 232 transmit the data from the X-ray detector(s) 222 to the data acquisition system 230. The data acquisition system 230 forms an image from the data and may store, display (e.g., on the display 233), and/or transmit the image. For example, the various embodiments may include an image reconstruction module 236, which may be implemented in hardware, software, or a combination thereof, that allows the data acquisition system to reconstruct images using X-ray data (e.g., radiographic or tomosynthesis data) acquired from the X-ray detector(s) 222 and as described in more detail herein.

Computed Tomography Scanner Overview—Computing Device

Figure 3:
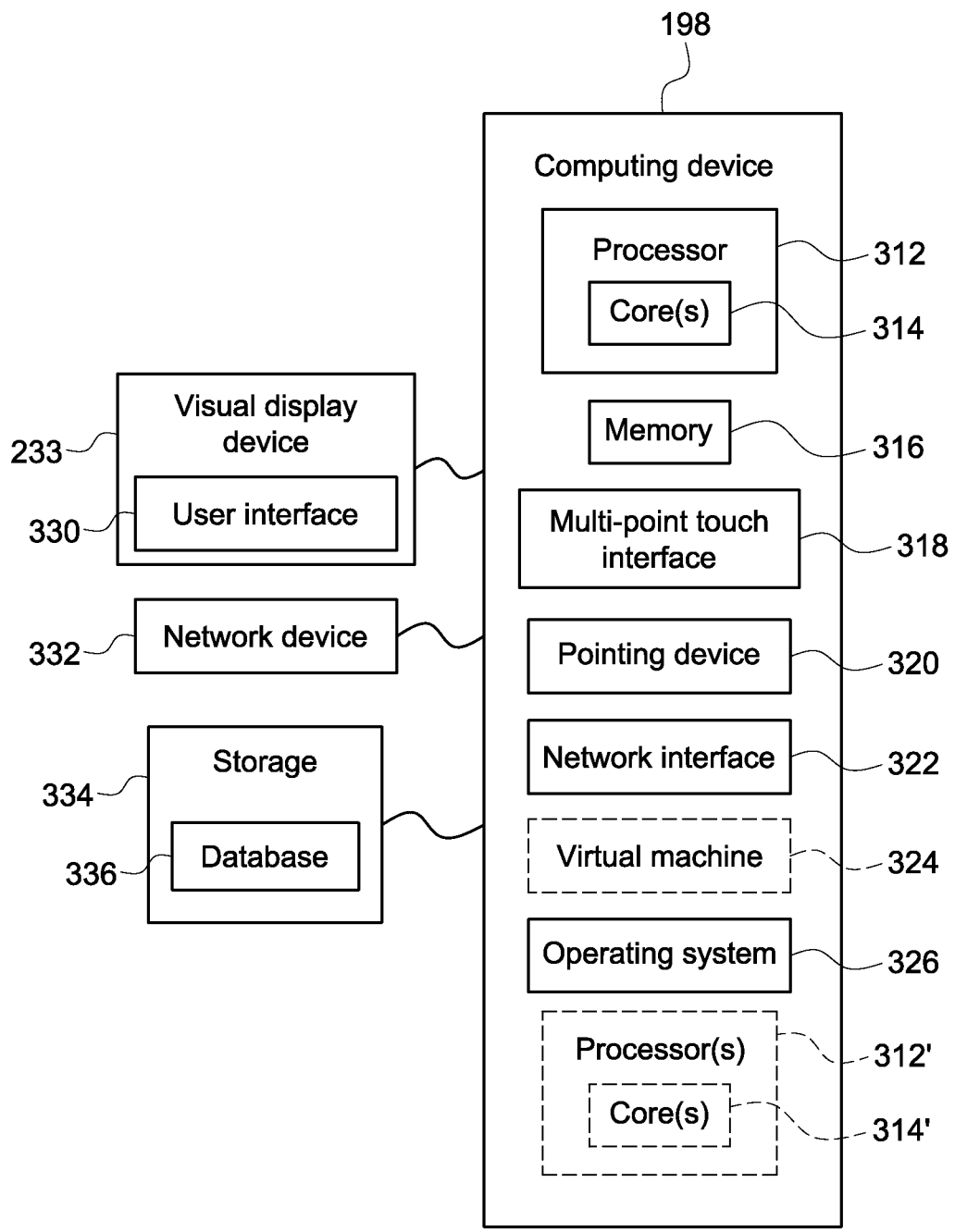
FIG. 3 is an exemplary computing device which may be programmed and/or configured to operate, for example, the system of FIGS. 1A,B and may also be used to implement certain processes described in relation to various embodiments of the present disclosure.

In some embodiments computer 198 may control the operation of the system 170 and may implement various aspects of the disclosed embodiments. FIG. 3 is a block diagram of an exemplary computing device 198 such as may be used in certain embodiments. The computing device 198 may include one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 316 included in the computing device 198 may store computer-readable and computer-executable instructions or software for interfacing with and/or controlling an operation of the scanner system 170. The computing device 198 may also include configurable and/or programmable processor 312 and associated core 314, and optionally, one or more additional configurable and/or programmable processing devices, e.g., processor(s) 312' and associated core(s) 314' (for example, in the case of computer systems having multiple processors/cores), for executing computer-readable and computer-executable instructions or software stored in the memory 316 and other programs for controlling system hardware. Processor 312 and processor(s) 312' may each be a single core processor or multiple core (314 and 314') processor.

Virtualization may be employed in the computing device 198 so that infrastructure and resources in the computing device may be shared dynamically. A virtual machine 324 may be provided to handle a process running on multiple processors so that the process appears to be using only one computing resource rather than multiple computing resources. Multiple virtual machines may also be used with one processor.

Memory 316 may include a computer system memory or random access memory, such as DRAM, SRAM, EDO RAM, and the like. Memory 316 may include other types of memory as well, or combinations thereof.

A user may interact with the computing device 198 through a visual display device 233, such as a computer monitor, which may display one or more user interfaces 330 that may be provided in accordance with exemplary embodiments. Visual display device 233 may be the same as display system 204 in some embodiments. The computing device 198 may include other I/O devices for receiving input from a user, for example, a keyboard or any suitable multi-point touch interface 318, a pointing device 320 (e.g., a mouse). The interface 318 such as a keyboard and the pointing device 320 may be coupled to the visual display device 233. The computing device 198 may include other suitable conventional I/O peripherals.

The computing device 198 may also include one or more storage devices 334, such as a hard-drive, CD-ROM, or other computer readable media, for storing data and computer-readable instructions and/or software that interface with and/or control an operation of the scanner system 170 described herein and/or to implement exemplary processes and methods described herein. Exemplary storage device 334 may also store one or more databases for storing any suitable information required to implement exemplary embodiments. For example, exemplary storage device 334 can store one or more databases 336 for storing information, such as scan sequences, X-ray data, X-ray images, photon counts, estimation of electrical properties, electrical property maps, and/or any other information that can be used to implement exemplary embodiments of the present disclosure. The databases may be updated manually or automatically at any suitable time to add, delete, and/or update one or more items in the databases.

The computing device 198 can include a network interface 322 configured to interface via one or more network devices 332 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 322 may include a built-in network adapter, network interface card, PCMCIA network card, card bus network adapter, wireless network adapter, USB network adapter, modem or any other device suitable for interfacing the computing device 198 to any type of network capable of communication and performing the operations described herein. Moreover, the computing device 198 may be any computer system, such as a workstation, desktop computer, server, laptop, handheld computer, tablet computer, or other form of computing or telecommunications device that is capable of communication and that has sufficient processor power and memory capacity to perform the operations described herein.

The computing device 198 may run any operating system 326, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the operations described herein. In exemplary embodiments, the operating system 326 may be run in native mode or emulated mode. In an exemplary embodiment, the operating system 326 may be run on one or more cloud machine instances.

In exemplary embodiments, the CT system 170 can be configured and/or programmed to transmit instructions, commands, and/or requests to the computing device 198 to control the CT-scan components to perform scan sequences and can be programmed and/or configured to receive CT-scan data or CT-scan images from the computing device 198.

Detector Behavior

Certain of the present embodiments contemplate systems and methods for anticipating undesirable behavior in detector array 178 which may adversely affect the dynamic flux range of the detector system. Detector array 178 may comprise energy sensitive photon-counting detector pixel arrays such as Cadmium Zinc Telluride (CZT) or Cadmium Telluride (CdTe) detector arrays. Such a detector can have a limited useful detection flux range, causing it to experience photon pileup at a high detection flux, and poor signal to noise ratio at low detection flux. For example, some manufacturers may limit the counting rate of the detector's electronics in order to provide a more accurate energy measurement. Unfortunately, this may also cause the photon signals to have a significant time width and therefore to "pile up" at the detector. Pile up may occur when photons arrive at the detector cells too close in time, resulting in two or more photons being counted as a single photon. Additionally, the energy distribution at the detector will be incorrect during pile up as it will have the summed energy of the two or more photons. A detector saturated in this manner may fail to count subsequently incident photons, thereby producing a photon count which is lower than the number of photons actually received. Like "pile up", other defects may more greatly influence the detected photon count at different photon fluxes than others. For example, some detector pixels may perform in an unstable manner at high incident flux, but perform well at lower incident flux. With a CZT or CdTe detector, for example, this unstable behavior may be related to crystal-lattice defects within the detector crystal. At high flux, these defects may accrue a time varying space charge that causes unstable behavior. Additional phenomenon, such as cosmic or industrial sources of X-rays, may also adversely affect photon counts of lower fluxes.

Detector systems having these features are referred to as "limited dynamic range" detectors herein. Such detectors, as discussed in greater detail below with reference to FIG. 4, may experience reduced signal to noise ratios at low detection fluxes and photon pileup at higher detection fluxes.

Figure 4:
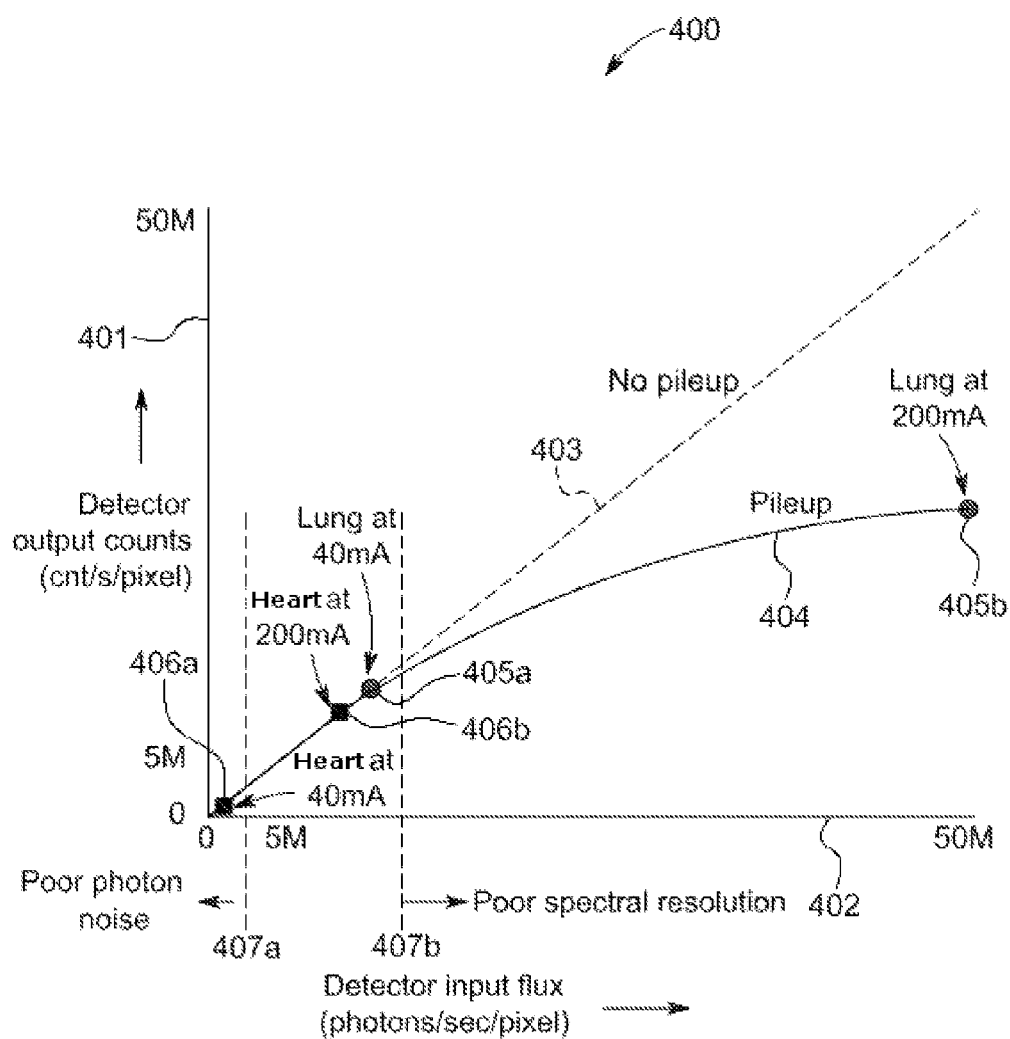
FIG. 4 is a plot depicting the relationship between detector output counts as a function of detector input flux for a given detector system.

FIG. 4 is a plot 400 depicting the relationship between detector cell output flux (counts/second/detector cell) 401 and detector cell input flux (photons/second/detector cell) 402 for certain detector systems. In the ideal relation, 403, the detector cell outputs a count to the system for each incident photon. Many real-world detectors, however, may exhibit a "limited dynamic range" behavior as discussed above. A "limited dynamic range" detector cell may generally experience photon pileup at higher detection fluxes and poor signal to noise ratio at lower detection fluxes.

The non-ideal relation 404 of certain "limited dynamic range" detector cells is depicted in FIG. 4. As the incident photon flux 402 increases, the detector cell outputs fewer and fewer photon counts than would be expected in the ideal relation 403. On the other hand, at lower fluxes, the photon count may become noisy and this may have an increasingly adverse effect on the reconstructed image quality. The limited dynamic range may be a consequence of defects in the detector apparatus, the X-ray source, or in their behavior at different times. Generally, for a single emission-detection event (sometimes referred to as a view period, in conventional CT-imaging jargon), each detector cell at the detector may operate at a point on the relation 404 depending on both source emission flux and attenuation of the flux as a consequence of the intervening object/patient. In some embodiments, an attenuation value may be determined from a look-up table relating the detected flux to an attenuation value. The look-up table may consider air measurements as described herein. Some embodiments may calculate the attenuation value using a formula, or relation, receiving the detection flux as input. The attenuating effect of the object/patient may depend on the energy distribution of the emitted photons.

The ability of the system to determine the attenuation may depend on the number of photons emitted. For example, certain anatomical features will attenuate the photon stream differently than other anatomical features. As indicated in FIG. 4, when the generator 190 operates X-ray source 174 at 40 mA (a low emission flux), the human heart may appear at the position 406a on the plot while the human lung may instead appear at the position 405a. This is to be expected as the heart is substantially full of dense blood and the lung is substantially full of less dense air. Thus, more photons pass through the lung than the heart. When the X-ray source operates at 200 mA (a high emission flux), the heart now appears in the desirable detection range at position 406b as more photons reach the detector. In contrast, too many photons pass through the air in the lung, and the lung appears in the undesirable range at position 405b. As indicated by this example, a high flux scan may yield detector over-ranging in detector cells where object attenuation is low. Conversely, a low flux scan may yield good detector values where the high flux scan over-ranged.

Thus, certain detector input fluxes may appear in undesirable regions of the plot 400. As mentioned above, random "noise" or general poor low-flux detector performance may adversely affect the count in the region below the position 407a. Similarly, pile-up or general poor high-flux detector performance may adversely affect the count in the region above position 407b. Certain of the present embodiments contemplate varying the X-ray source current and/or source voltage, or varying some other form of source intensity and/or spectrum modulator, between various values and then filtering the detected photon counts at a detector cell 224, or the detector as a whole, based on the incident detector flux. In this manner more reliable detector counts may be determined and used to generate a more accurate image.

Various Detection Improvements

Generally, an X-ray image of an object may be derived from the object's attenuation of the photon flux between the source and detector. The attenuation may be determined by measuring the detected flux both with and without the object in the path between the source and detector, while insuring that the source emitted flux (and the source-detector separation distance, etc.) is the same in both cases. Measurement without the object may be referred to as a calibrating detector flux measurement, or "air measurement". The "air measurement" may be measured separately from the imaging of the object and may be stored in the system's memory. In some embodiments, the "air measurement" may be taken once, and used during the imaging of many different objects.

In embodiments which consider an "air measurement", the attenuation may be calculated as the ratio of the detected flux with object present to the detected flux when the object is not present (e.g., the "air measurement"). As air is generally less dense than an imaged object, using the source emitted flux when imaging an object for the "air measurement" may result in saturation of the detector and unusable values. Consequently, the flux emitted during the "air measurement" may be much less than the source emitted flux used when imaging an object. Because of this, certain embodiments contemplate associating different "air measurement" values for different source emission fluxes when imaging an object. In each instance the "air measurement" may be scaled to properly correlate with the corresponding emission flux.

Figure 5:
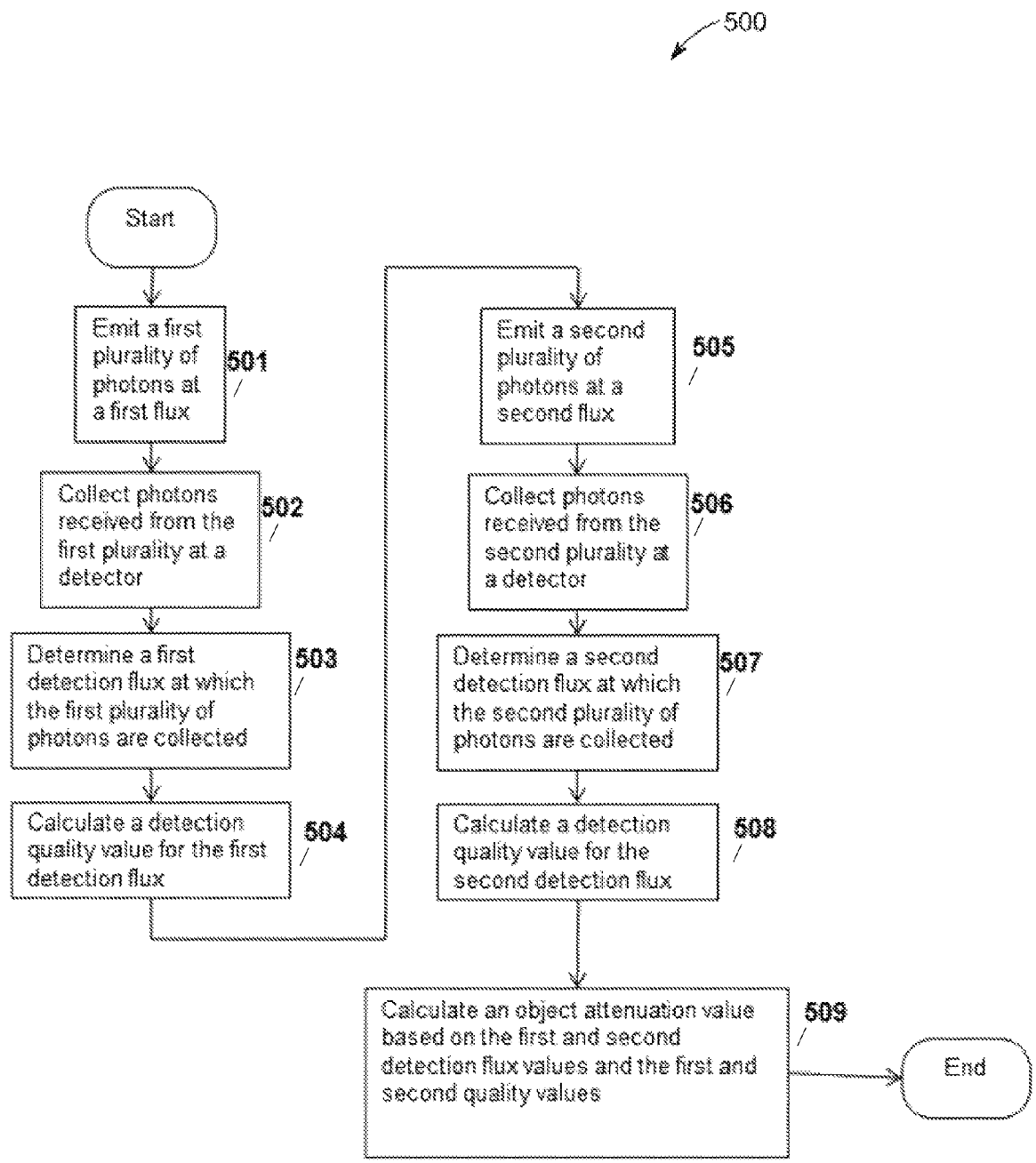
FIG. 5 is a flowchart of an exemplary method for improving detector efficiency as contemplated in certain embodiments.

FIG. 5 depicts a method 500, in accordance with certain embodiments of the invention, for improving attenuation values generated using a dynamic range-limited detector as discussed with respect to FIG. 4. The method may ensure that detector output counts are only considered, or are given more deference, when the detector input flux falls within the range between positions 407a and 407b as indicated in the plot of FIG. 4. In some embodiments, the range between positions 407a and 407b may be defined by a reference flux value, such as the midpoint between positions 407a and 407b. Either of the boundary positions 407a-b of the range could also constitute a reference flux. The distance from the reference flux may then be used to determine whether an incident flux falls within the range, or how much weight should be accorded to the photon count associated with the incident flux when calculating an object attenuation value.

The method 500 may be applied for each detector cell and for each source emission when imaging an object. The method 500 may begin at block 501 by emitting a first plurality of photons from an X-ray source at a first flux. For example, the system may operate the X-ray source at 40 mA as indicated in FIG. 4. The 40 mA current, introduced at generator 190, may produce a corresponding number of detected photons that depict the heart at position 406a and the lung at position 405a. The detector array 178 may be simultaneously, previously, or subsequently activated at block 502 to receive the photons emitted at block 501. Based on the photon counts measured for each detector cell and each source emission, the system may determine at block 503 the flux 402 incident on the detector cell. Block 503 may include use of detector calibration data (not shown) and/or air measurement values associated with the first source emission flux. At block 504 the system may determine a quality value for the detector measurement. A quality value may indicate how close the detection flux is to the range between 407a and 407b. For example, the quality value associated the lung at position 405b at 200 mA may receive a low quality value or 0, while the lung at position 405a may receive a high quality value. In some embodiments, the quality value may fall between 0 and 1. Fluxes within the region between 407a and 407b may receive a quality value of 1. Fluxes outside the region may receive decreasingly smaller quality values or simply 0. In other embodiments, fluxes at the midpoint of the region between 407a and 407b will receive a quality value of 1, while fluxes further from the midpoint will receive smaller and smaller values (e.g., by a linear or Gaussian distribution). In still other embodiments, a quality value may be the inverse of the absolute value of the difference between the measured detection flux value and the midpoint of the specified range. The weight associated with a quality value could be calculated simply as the quality value itself and the final attenuation value could be calculated as the weighted sum of attenuation values based on their corresponding quality values. The quality value may be based on either the detector photon count from block 502, or the detection flux from block 503.

Although the embodiment described in relation to FIG. 4 discusses generation of a flux in terms of source current, one will recognize that the detected flux may also be increased/decreased by altering the X-ray source voltage, and consequently the energy distribution of the emitted photons. That is, one way to achieve a higher detection flux is to emit more photons with a higher X-ray source flux, but another way is to adjust the properties of the emitted photons, e.g. the mean energy, so that more photons are able to reach the detector through the object/patient being imaged. The detected flux may also be increased/decreased by altering the X-ray attenuation or filtration between the source and detector.

The method 500 may then repeat the steps 501, 502, 503, 504 but at a higher (or lower) emission flux at the X-ray source, as depicted in blocks 505, 506, 507, 508. For example, the system may emit photons at 40 mA at block 501 and 200 mA at block 504 as indicated in FIG. 4. As discussed, the higher 200 mA current will produce a greater number of photons than at 40 mA and the system will consequently depict the heart at position 406b and the lung at position 405b. The system may collect these photons at block 505 and determine the detection flux at which the second set of photons are collected 506.

At block 509 the system may then determine an attenuation value to be used when creating an image. The operation in block 509 may occur in some embodiments in either the data acquisition system 230 or image reconstruction module 236, although one will recognize a plurality of other locations where the operation may occur. In certain embodiments, the determination at block 509 will consider the attenuations associated with each of the first and second detection flux values in proportion to their corresponding quality value.

At block 509, certain embodiments contemplate calculating the attenuation separately for all detection flux values and associated air measurement values, assign each attenuation value a weight based on the associated quality value, then sum the weighted attenuation values and divide by the sum of the weights. In some embodiments, the data acquisition system 230 or image reconstruction module 236 may use various ancillary information to correct for other detector or system aberrations. There are many ways to calculate the object attenuation on the path between the source and a detector element using the multiple source emission levels and associated detector-flux measurements.

The process specified by blocks 501, 502, 503, and 504 may be generalized in some embodiments to more than two source emission levels. The measured detector flux values, the quality values, and the associated air measurement values may be considered at block 509 to calculate an object attenuation value. Although reference may be made to a single detector or X-ray source, one will additionally recognize that the system may employ a plurality of X-ray sources or a plurality of detectors to perform the same or similar functions. A single X-ray source may correspond to one or more detectors and vice versa. One will also recognize that a single detector may include thousands or millions of detectors cells, and one may arbitrarily divide collections of cells into one or more detectors. One will recognize that the process 500 of FIG. 5 may be performed separately for each of the detector cells.

That is, for a detector comprising N detector cells, the process 500 would be performed N times for each X-ray projection (i.e., for each final attenuation calculation across the entire detector array). With a typical CT X-ray system, the system gantry may be continuously rotating. Thus, the path between the X-ray source-point and any detector element may be constantly changing. If the different source emissions in process 500 are executed sequentially in time, then these slight path changes may either be ignored, or be accounted using various spatial interpolation methods known to one skilled in the art. Alternatively, the different source emissions in process 500 may be executed on different gantry rotations. In that case, motion of the patient or object (e.g., a beating heart) may be included in the measurement process.

Detection Start Time Considerations

Figure 6:
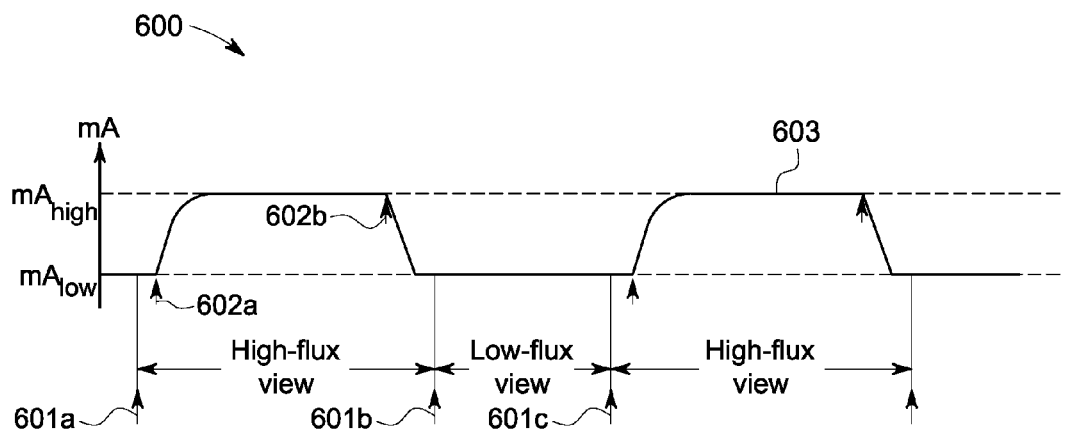
FIG. 6 is a timing diagram depicting the current waveform in the CT-scan system X-ray source and the corresponding detection intervals for the respective fluxes.

FIG. 6 is a timing diagram depicting the current waveform 603 at the X-ray source and the corresponding detection intervals for the high (the interval 601a to 601b) and low (the interval 601b to 601c) fluxes. In many embodiments, the flux transitions cannot be made instantaneous by the system 170. Instead, as depicted in FIG. 6, there will be a non-zero time associated with each low-to-high transition 602a and each high-to-low transition 602b. The onsets 602a-b may be caused by activating or deactivating a current switch. As the high-flux detection is less likely to be adversely affected by these transitions than the low-flux detection, certain embodiments contemplate placing the flux transition entirely within the higher flux view period. That is, the detector is activated for the high-flux detection between positions 601a and 601b so as to encompass the current transitions from low to high and high to low current. Conversely, the detector is activated for the low-flux detections between 601b and 601c while the waveform is in steady state. In these embodiments, this may avoid contamination of the lower flux period by pileup effects that occur during the transitions' higher flux values.

Source Voltage Perturbation Considerations

Figure 7:
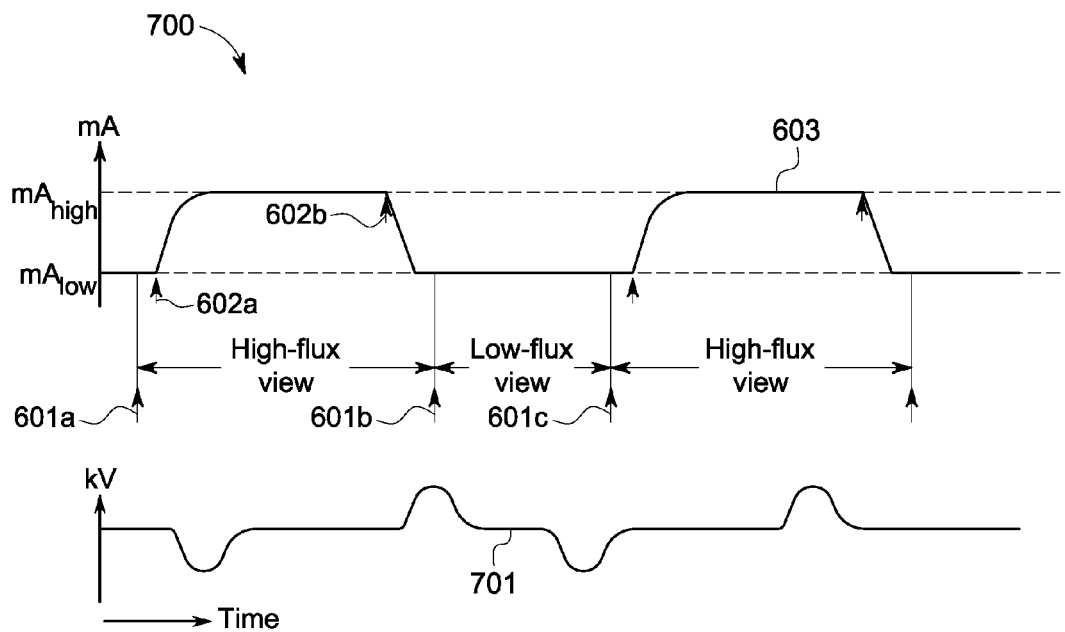
FIG. 7 is a timing diagram as in FIG. 6, additionally depicting possible perturbations in the X-ray source voltage.

FIG. 7 is a timing diagram as in FIG. 6, additionally depicting possible perturbations in the X-ray source voltage 701 occurring as a consequence of current switching between high and low values. As discussed above, certain CT systems may measure not only the number of incident photons, but their energy at the detector array 178 as well. Distortions in the X-ray source voltage may adversely affect the energy readings at the detector. With knowledge of the variations in the emission spectrum, reconstruction of the imaged object could be greatly improved.

Fortunately, as depicted in FIG. 7, the distortions in the voltage perturbations 701 may be consistent from view to view. In fact, the average spectrum may be the same for each low flux emission-detection event (the points 601b to 601c) and for each high flux emission-detection event (the points 601a to 601b). The emission spectrums may be measured, inferred, or simulated/calculated during calibration in some embodiments. Emission spectrums may also be inferred using a real-time reference detector. The real-time reference detector may include a number of detector cells whose absorption pattern is unaffected by the object under study. For example, these "reference" detector cells may always have a direct line of sight to the X-ray tube (source). Known absorption elements or thicknesses may also be placed in the path of the detector. By using different known absorption elements or thicknesses, one can infer the emission spectrum.

Source-Voltage Manipulation During mA Switching

Figure 8:
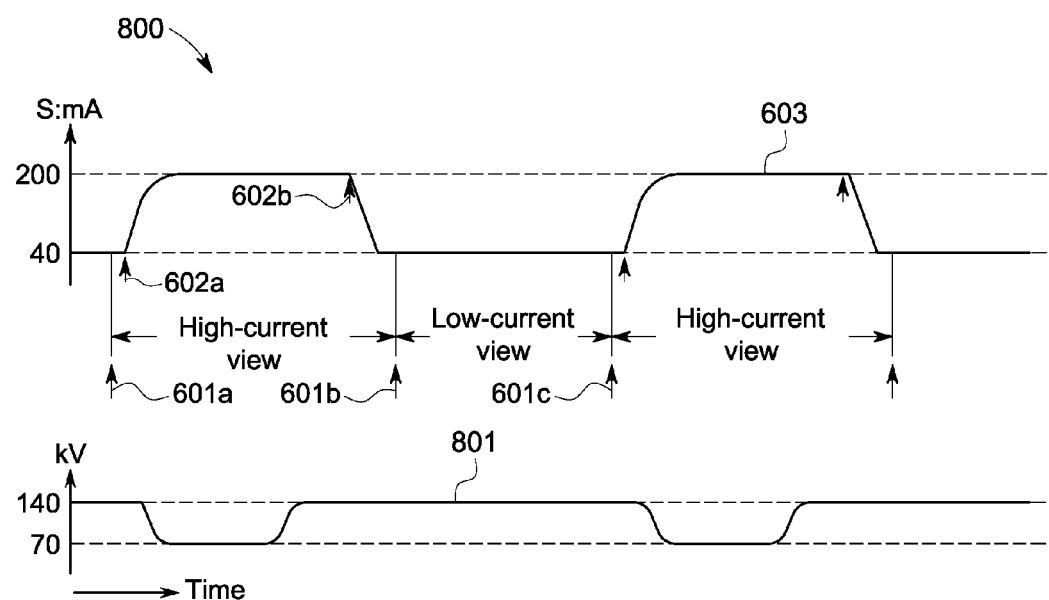
FIG. 8 is a timing diagram as in FIG. 6, additionally depicting intentional modulation of both photon energy (such as by adjusting the X-ray source voltage) and the photon rate (such as by adjusting the X-ray source current).

FIG. 8 is a timing diagram as in FIG. 6, but additionally depicting a step change in the X-ray source voltage. By changing the source voltage in synchrony with the view period, low-current and high-current views may advantageously have different energy spectrums. The average spectrum over any view period can be further controlled by controlling the values and duty cycle of the high and low voltages during the view, or by changing the voltage in any desired manner during the view. Current and voltage transitions may be synchronized to simplify spectral calibration of the system. In some embodiments, it may be advantageous to insert small delays between voltage and current changes. These delays may limit the peak flux received during any view by lowering the current before increasing the voltage or conversely lowering the voltage before increasing the current.

General Considerations

Certain embodiments further contemplate applying different flux settings for each patient exposure/scan. In some embodiments, there may be multiple sequential views at each flux setting. These views may have the same or different durations. In some embodiments the pattern of flux settings may repeat during the entire exposure/scan. Alternatively, the exact flux settings and/or view periods of each view may be adapted during the scan (with or without gantry rotation), either from pre-acquired data, or dynamically using feedback during the scan. In some embodiments, the flux settings may be adapted by changing either tube current, tube voltage, or any combination of both.

In some embodiments implementing fast flux switching, the flux may be switched within each gantry rotation, or between successive gantry rotations. In these embodiments the data at low and high flux may either be acquired during a single scan, or during individual successive scans. Switching flux rapidly between successive views during a patient scan may reduce movement artifacts. It may also advantageously measure the spectrum for each view. One may introduce several elements (e.g. with different spectral filtration, and/or different detector cell sizes), in order to ensure that the system can accurately measure the spectrum at each flux setting.

In some embodiments a reference detector may be used to calibrate the system operation. The system may normalize acquired data based upon the reference detector measurement. This may significantly reduce system calibration time, as the exact spectrum during the scan may not need to be known in advance. This may also reduce the accuracy requirements for the high-voltage generator. Implementing a reference detector may also allow the system to more loosely control the exact spectrum during each view, as it allows normalization to the actual spectrum of each view. The reference detector may be used for real-time feedback of the spectrum and/or dosage, in order to dynamically adapt the spectrum and/or flux to the patient anatomy during the scan.

Further variations will also be recognized based on the above disclosure. For example, an X-ray attenuator may be placed between the X-ray source and the patient to compensate for the detector's limited dynamic range. The attenuator may filter the emitted photons to compensate for the detectors' behavior. Wrapping the object/patient to be observed in a water jacket, or similar fluidic chamber, may also serve to attenuate X-rays based on the detector's limitations.

Though the system 170 in FIG. 1 may be depicted with single pairs of operating elements for purposes of explanation, one will recognize that some systems may have a plurality of elements where only one is shown. For example, a system may have more than one X-ray source 174 and more than one detector array 178. Each detector array may be paired with one or more X-ray sources, or a single X-ray source may be used in conjunction with a plurality of detector arrays.

Remarks

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

We claim:

1. A method to accommodate detector behavior when generating at least a portion of an X-ray image comprising:
    emitting a first plurality of photons;
    collecting at a detector at least some of the first plurality of photons at a first detection flux;
    emitting a second plurality of photons;
    collecting at the detector at least some of the second plurality of photons at a second detection flux, wherein the second detection flux is greater than the first detection flux, and wherein an average spectrum of the first detection flux and the second detection flux is substantially similar;
    determining a first quality value associated with an anatomical feature of interest, wherein the first quality value indicates whether the first detection flux falls within a detection range for the anatomical feature of interest;
    determining a second quality value associated with the anatomical feature of interest, wherein the second quality value indicates whether the second detection flux falls within the detection range for the anatomical feature of interest;
    determining a first attenuation value associated with the first detection flux;
    determining a second attenuation value associated with the second detection flux; and
    generating at least a portion of an X-ray image based on the first attenuation value if the first detection flux falls within the detection range and generating at least a portion of the X-ray image based on the second attenuation value if the second detection flux falls within the detection range,
    wherein the first quality value indicates whether the first detection flux is proximate a midpoint of the detection range, and wherein the second quality value indicates whether the second detection flux is proximate the midpoint of the detection range, and
    wherein the first quality value is associated with a first weighting factor based on a difference between the first flux and the midpoint of the detection range, and wherein the second quality value is associated with a second weighting factor based on a difference between the second flux and the midpoint of the detection range, and
    wherein generating at least a portion of an X-ray image comprises determining a final attenuation value, the final attenuation value is based on the first attenuation value associated with the first detection flux weighted by the first weighting factor and the second attenuation value associated with the second detection flux weighted by the second weighting factor.

2. The method of claim 1, wherein the detector is configured to experience:
    photon pileup at a high detection flux, the high detection flux greater than a reference flux; and
    a signal to noise ratio at a low detection flux less than a signal to noise ratio at the reference flux, the low detection flux less than the reference flux.

3. The method of claim 1, wherein emitting the first plurality of photons comprises applying a source attenuator in a first configuration and wherein emitting the second plurality of photons comprises applying the source attenuator in a second configuration, the second configuration different from the first configuration.

4. The method of claim 1, wherein first plurality of photons are emitted using a first current and the second plurality of photons are emitted using a second current, the first current different from the second current.

5. The method of claim 1, further comprising beginning the collection of the at least some of the second plurality of photons before increasing a current associated with emitting the second plurality of photons.

6. The method of claim 1, further comprising stopping the collection of the at least some of the second plurality of photons after decreasing a current associated with emitting the second plurality of photons.

7. The method of claim 1, wherein the second plurality of photons is emitted before the first plurality of photons is emitted.

8. A non-transitory computer-readable medium comprising instructions configured to cause one or more processors to cause a system to:
    emit a first plurality of photons;
    collect at a detector at least some of the first plurality of photons at a first detection flux;
    emit a second plurality of photons;
    collect at the detector at least some of the second plurality of photons at a second detection flux, wherein the second detection flux is greater than the first detection flux, and wherein an average spectrum of the first detection flux and the second detection flux is substantially similar;
    determine a first quality value for an anatomical feature of interest, wherein the first quality value indicates whether the first detection flux falls within a detection range for the anatomical feature of interest;
    determine a second quality value for the anatomical feature of interest, wherein the second quality value indicates whether the second detection flux falls within the detection range for the anatomical feature of interest;
    determine a first attenuation value associated with the first detection flux;
    determine a second attenuation value associated with the second detection flux; and
    generate at least a portion of an X-ray image based on the first attenuation value if the first detection flux falls within the detection range and generating a least a portion of the X-ray image based on the second attenuation value if the second detection flux falls within the detection range, wherein the first quality value indicates whether the first detection flux is proximate a midpoint of the detection range, and wherein the second quality value indicates whether the second detection flux is proximate the midpoint of the detection range, and wherein the first quality value is associated with a first weighting factor based on a difference between the first flux and the midpoint of the detection range, and wherein the second quality value is associated with a second weighting factor based on a difference between the second flux and the midpoint of the detection range, and wherein generating at least a portion of an X-ray image comprises determining a final attenuation value, the final attenuation value is based on the first attenuation value associated with the first detection flux weighted by the first weighting factor and the second attenuation value associated with the second detection flux weighted by the second weighting factor.

9. The non-transitory computer-readable medium of claim 8, wherein generating at least a portion of an X-ray image comprises using the at least some of the first plurality of photons to generate the first attenuation value if the first detection flux falls within the detection range.

10. A system to accommodate detector behavior when generating at least a portion of an X-ray image comprising:
a first X-ray source configured to emit a first plurality of photons;
a second X-ray source configured to emit a second plurality of photons, the second plurality of photons comprising more photons than the first plurality of photons;
a first detector configured to receive at least some of the first plurality of photons; a second detector configured to receive at least some of the second plurality of photons;
a first flux determiner configured to determine a first flux at which the at least some of the first plurality of photons are collected at the first detector;
a second flux determiner configured to determine a second flux at which the at least some of the second plurality of photons are collected at the second detector;
one or more computer systems configured to:
determine a first quality value for an anatomical feature of interest, wherein the first quality value indicates whether the first detection flux falls within a detection range for the anatomical feature of interest, wherein an average spectrum of the first detection flux and the second detection flux is substantially similar;
determine a second quality value for the anatomical feature of interest, wherein the second quality value indicates whether the second detection flux falls within the detection range for the anatomical feature of interest;
determine a first attenuation value associated with the first detection flux; determine a second attenuation value associated with the second detection flux; and
generate at least a portion of an X-ray image based on the first attenuation value if the first attenuation flux falls within the detection range and generating at least a portion of the X-ray image based on a the second attenuation value if the second detection flux falls within the detection range, wherein the first quality value indicates whether the first detection flux is proximate a midpoint of the detection range, and wherein the second quality value indicates whether the second detection flux is proximate the midpoint of the detection range, and wherein the first quality value is associated with a first weighting factor based on a difference between the first flux and the midpoint of the detection range, and wherein the second quality value is associated with a second weighting factor based on a difference between the second flux and the midpoint of the detection range, and wherein generating at least a portion of an X-ray image comprises determining a final attenuation value, the final attenuation value is based on the first attenuation value associated with the first detection flux weighted by the first weighting factor and the second attenuation value associated with the second detection flux weighted by the second weighting factor.

11. The system of claim 10, wherein at least one of the first detector and the second detector is configured to experience:
photon pileup at a high detection flux, the high detection flux greater than a reference flux; and
a signal to noise ratio at a low detection flux less than a signal to noise ratio at the reference flux, the low detection flux less than the reference flux.

12. The system of claim 10, wherein the first X-Ray source and the second X-Ray source are the same X-Ray source, the first detector and the second detector are the same detector, and the first flux determiner and the second flux determiner are the same flux determiner.

* * * * *